United States Patent
Wolfgang et al.

(10) Patent No.: US 7,456,306 B2
(45) Date of Patent: Nov. 25, 2008

(54) STEARATE COMPOSITION AND METHOD OF PRODUCTION THEREOF

(75) Inventors: Steven M. Wolfgang, Glen Carbon, IL (US); Todd P. Heider, St. Louis, MO (US)

(73) Assignee: Mallinckrodt Inc, Hazelwood, MO (US)

( * ) Notice: Subject to any disclaimer, the term of this patent is extended or adjusted under 35 U.S.C. 154(b) by 322 days.

(21) Appl. No.: 10/558,591

(22) PCT Filed: Jul. 28, 2004

(86) PCT No.: PCT/US2004/024485

§ 371 (c)(1), (2), (4) Date: Nov. 29, 2005

(87) PCT Pub. No.: WO2005/011641

PCT Pub. Date: Feb. 10, 2005

(65) Prior Publication Data

US 2006/0247456 A1    Nov. 2, 2006

Related U.S. Application Data

(60) Provisional application No. 60/490,596, filed on Jul. 28, 2003.

(51) Int. Cl.
*C07C 51/43* (2006.01)
(52) U.S. Cl. .................................................. 554/195
(58) Field of Classification Search .................. None
See application file for complete search history.

(56) References Cited

U.S. PATENT DOCUMENTS

| | | | |
|---|---|---|---|
| 2,313,844 A | 3/1943 | Sullivan | |
| 3,876,551 A | 4/1975 | Laufer et al. | |
| 4,731,195 A | 3/1988 | Olson | |
| 4,777,080 A | 10/1988 | Harris, Jr. et al. | |
| 4,800,082 A | 1/1989 | Karbowski et al. | |
| 5,032,632 A | 7/1991 | Saxton | |
| 5,175,322 A | 12/1992 | Yoshizawa et al. | |
| 5,277,832 A | 1/1994 | Gill et al. | |
| 5,364,610 A | 11/1994 | Merris, Jr. | |
| 5,434,277 A * | 7/1995 | Hwu et al. | 554/71 |
| 5,447,729 A | 9/1995 | Belenduik et al. | |
| 5,631,215 A | 5/1997 | Kinsman | |
| 5,952,004 A | 9/1999 | Rudnic et al. | |
| 6,395,701 B1 | 5/2002 | Connor et al. | |
| 6,437,000 B1 | 8/2002 | Mulye | |
| 6,699,403 B2 | 3/2004 | Dluzenski et al. | |
| 2002/0052411 A1 | 5/2002 | Gobel et al. | |
| 2002/0187536 A1 | 12/2002 | Kulkarni et al. | |
| 2004/0092418 A1 | 5/2004 | Connor et al. | |
| 2004/0092419 A1 | 5/2004 | Connor et al. | |
| 2004/0124397 A1 | 7/2004 | Dluzneski et al. | |

FOREIGN PATENT DOCUMENTS

| WO | WO 01/05430 A1 | 1/2001 |
|---|---|---|
| WO | WO 03/011214 A2 | 2/2003 |

OTHER PUBLICATIONS

D. Beckers & S. Prugovecki, Investigation of the structural stablility of magnesium stearate . . . , downloaded Dec. 13, 2005 from www.dxcidd.com/01/0pdf/D-036.pdf.
Friedrich, Steffens, Beck & Sievers, Influence of magnesium . . . , downloaded Dec. 13, 2005 from www.pharmtech.uni-bonn.de/download/Veroeffentlichungen/friedrichAPV2002.pdf.
Koivisto, Jalonen & Laine, The effect of moisture and degassing on some physical . . . , downloaded Dec. 13, 2005 from www.physics.utu.fi/industrial/pdf/koivisto1.pdf.
Steffens & Koglin, The magnesium stearate problem, Mfg. Chem., 1993, p. 16, 17, 19.
Swaminathan & Kildsig, An examination of the moisture sorption characteristics of commercial magnesium stearate, AAPS PharmSciTech, 2001, 2 (4) article 28.

* cited by examiner

*Primary Examiner*—Deborah D Carr

(57) ABSTRACT

An improved alkali earth metal stearate composition is disclosed and is prepared by reacting a fatty acid component including at least about 80% by weight stearic acid and at least about 5% by weight palmitic acid with an alkali hydroxide to form an alkali soap. An aqueous metal salt solution is then added to the soap to form the improved alkali earth metal stearate. The improved alkali earth metal stearate includes a significant amount of the dihydrate form of the stearate.

21 Claims, No Drawings

STEARATE COMPOSITION AND METHOD OF PRODUCTION THEREOF

CROSS REFERENCE TO RELATED APPLICATIONS

This application is a national stage application of PCT/US04/024485, filed Jul. 28, 2004, which claims the benefit of U.S. Provisional Application No. 60/490,596, filed Jul. 28, 2003.

BACKGROUND OF INVENTION

This invention relates to the industrial manufacture of alkali earth metal stearate compositions useful as industrial lubricants for uses including metal forming and tablet formulation of pharmaceutical preparations. More particularly, this invention relates to a process for preparing magnesium stearate lubricant exhibiting improved properties in lubrication and dissolution of pharmaceutical preparations in tablet form.

Numerous patents disclose the utility of stearates as lubricants or powder flow enhancers. U.S. Pat. Nos. 6,437,000, 5,032,632, 5,952,004, 5,447,729, 4,800,082, 4,777,080 and Published Application 2002/0052411 provide typical disclosures of such utility.

The use of magnesium stearate as a pharmaceutical tableting lubricant is well known in the art. According to USP/NF (2004), magnesium stearate is described as a substance containing at least 40% stearic acid, 90% as the sum of stearic acid and palnitic acid, and not more than 6.0% water. Magnesium stearate commonly used in pharmaceutical applications is a mixture of magnesium stearate and magnesium palmitate, since sources used to derive magnesium stearate include tallow, fat, palm oil, and soybean oil, all of which are glyceryl esters of $C_{16}$ and $C_{18}$ fatty acids. Moreover, the state of magnesium stearate may be amorphous, or exhibit any of the following crystalline forms—anhydrous, monohydrate, dihydrate, and trihydrate. The USP/NF description of the composition and attributes of magnesium stearate does not account for functionality differences of the various crystalline forms. Further, the water content of up to 6.0% allows for products containing many possible combinations of hydrated forms that meet the requirements in the compendial monograph.

Pharmaceutical manufacturers and researchers have found that of the three polymorphic hydrates (mono-, di- and tri-), the dihydrate form is preferred as it provides superior lubricating properties. It is also known that the content of water and the resulting crystal forms contribute to functionality of magnesium stearate. Magnesium stearate compositions that contain some dihydrate are perceived to have advantages in the formulation and manufacture of solid dosage forms. It has been reported that improvements—in disintegration, dissolution, crush strength and extrusion force are related specifically to the presence of dihydrate as opposed to other hydrated forms of magnesium stearate. Dihydrate have been reported to have the best anti-caking properties.

However, the prior art has failed to describe the composition in terms of its stearic acid/palmitic acid content, nor a method for preparing it. Commercial fatty acids do not necessarily have the correct composition to obtain pure dihydrate, and the lack of consistency in their compositions make controlling the content of dihydrate in the finished product challenging. The dihydrate is not an intermediate substance in the formation of the trihydrate from the anhydrous form when it was exposed to high humidity, and is only crystallized from solution under certain circumstances.

Further, currently available magnesium stearate compositions have the potential to adversely affect pharmacological activity by providing a water repellant barrier to dissolution of drugs, and can have a major influence on bioavailability, particularly of sustained release drugs.

In order for the pharmaceutical industry to gauge the potential benefits of the dihydrate form for the purpose of creating new formulations based on these findings, pure or at least well-defined compositions containing dihydrate material must ultimately become commercially available.

Commercially available magnesium stearate is actually a mixture of magnesium stearate and palmitate, and the hydration and degree of crystallinity vary significantly depending upon the manufacturing process, as well as from batch to batch depending on the starting materials. While high-purity forms of magnesium stearate dihydrate that have been prepared and characterized in the laboratory, there are no commercially viable methods for the preparation of the preferred dihydrate form.

Improvements and efficiencies in the industrial preparation of stearate salts have been the subject of considerable research. As the number and use of medications, particularly in tablet form, expands, so to does the demand for ingredients employed in pharmaceutical tablet formation as well as in industrial operations. One such industrial application is metalworking that has also increased demand for reasonable priced lubricants of the stearate class, as is found in U.S. Pat. No. 5,277,832.

Another attempt to gain efficiency and an improved product is disclosed in U.S. Pat. No. 5,175,322. This patent discloses a continuous process for manufacturing alkali metal stearate soaps by the double decomposition method wherein a stream of an alkali metal soap and an inorganic metal salt is dropped on a moving impeller of a mixer thereby instantaneously mixing the reactant together followed by rapid discharge from the reactor of the newly formed stearate salt. This process is purported to provide a product free of unreacted starting materials and unwanted by-products. An improved double decomposition reaction was disclosed in U.S. Pat. No. 5,434,277 wherein it is disclosed that such reactions do not provide high purity products because of the presence of unreacted starting materials present in the product. The solution to this problem according to this disclosure is to provide alternated basification-acidification of the reaction mixture. The effectiveness of the alternate treatment of the reaction mixture was shown by DSC analysis of the product indicating the disappearance of stearic-acid starting material after alternative treatment.

A publication entitled "The Magnesium Stearate Problem" originally presented as a paper in 1992 and then published in Manufacturing Chemist, December 1993 discloses a study of the variations in lubricant properties of products from various industrial batches of stearate that has been observed in the industry. The observed variations were reported by K. J. Steffens and J. Koglin in an attempt to determine the unexplained cause of performance variation of seemingly identically produced industrial production batches of stearate salt. The variations observed were with respect to lubrication and tablet properties.

It is therefore desirable to provide an alkali metal stearate composition and related method of production that result in consistent production of the dihydrate form of the alkali metal stearate.

SUMMARY OF INVENTION

An aspect of the present invention is to provide an improved alkali metal stearate composition comprised of the reaction product of at least one fatty acid in a basic solution with at least one alkali earth metal sulfate. The fatty acid is comprised of at least about 80% by weight stearic acid and at least about 5% by weight palmitic acid.

Another aspect of the present invention is to provide a method for preparing the improved alkali earth metal stearate composition. At least one fatty acid comprised of at least about 80% by weight stearic acid and at least about 5% by weight palmitic acid is added to a basic aqueous solution. At least one alkali earth metal sulfate is added, and the at least one alkali earth metal sulfate reacts with the at least one fatty acid to form the improved alkali earth metal stearate composition.

DETAILED DESCRIPTION

There is provided an improved alkali earth metal stearate composition and related method of preparation, wherein a substantial portion of the stearate is in the dihydrate form.

Methods of making metallic salts of fatty acids are well known in the art. The "double decomposition" method involves a two-step process. First, the fatty acid is reacted with at least one base, typically at least one alkali hydroxide to form an alkali soap. Second, at least one aqueous metallic salt solution is added to the soap to form metallic salts of the corresponding fatty acid.

Conventional pharmaceutical preparation of alkali earth metal stearates, for example magnesium stearate and calcium stearate, typically utilize this method. The stearic acid reacts with an alkali hydroxide, for example NaOH, to form the sodium soap, which then reacts with an alkali earth metal salt, for example magnesium chloride, as shown below:

$$2CH_3(CH_2)_{16}COOH+2NaOH \rightarrow \quad (1)$$

$$2C_{18}H_{35}O_2Na+MgCl_2 \rightarrow \quad (2)$$

$$C_{36}H_{70}O_4Mg+2NaCl \quad (3)$$

Stearate compositions produced by this method exhibit great variation in quality and properties. It is known that commercially available stearic acid typically contains palmitic acid also. While pure stearic acid does have limited availability, the purification is not feasible on a industrial scale.

It has now been determined, however, that this impurity (palmitic acid) can lead to the formation of an improved stearate composition. By manipulating the components of the stearic acid starting material, more specifically the ratio of stearic acid to palmtic acid, a significant amount of the dihydrate form of the stearate product can be formed. The dihydrate form of the stearate provides a product which is substantially crystalline, with substantial platelet formation, thought to be responsible for the improved lubricating properties and decreased interference with bioavailability observed with the stearate dihydrate.

In the present invention it has been determined that a fatty acid component of at least about 80% by weight stearic acid and at least about 5% by weight palmitic acid, with 88% by weight stearic acid to about 10% by weight palmitic acid being preferred; 90% by weight stearic acid to 8% by weight palmitic acid being more preferred; and about 93% by weight stearic acid to about 5% by weight palmitic acid being optimal.

In an alternative embodiment, in addition to using preferred compositions of stearic/palmitic acids, the water content of the stearic/palmitic acids is defined. In this embodiment, the composition disclosed is comprised of magnesium stearate palmitate dihydrate having a stearate/palmitate ratio of at least 10:1 and a total water content of less than about 6%. Of that 6% water, preferably 15-100% of the total water content is crystalline water dihydrate, with less than about 10% of the total water content being free water, and the remainder of the water content being monohydrate. The fatty acid used in this alternative embodiment contains the sum of stearate and palmitate no less than 98% of the total acid content. The water content and hydration state of the final product vary as the ratio of stearic acid/palmitic acid, pH and conditions of drying are varied. The desired dihydrate is most likely to form when the ratio of stearic acid/palmitic acid is >10, when the pH is closer to neutral and when the drying temperature does not exceed 60° C.

The composition disclosed in this alternative embodiment exhibits beneficial functionalities including improving powder flow characteristics, reducing ejection force/compression force ratio, and minimizing any retardation of disintegration and dissolution rates of hydrophobic, or poorly water soluble drugs such as dilantin, modafinil, zolpidem and alike, which are frequently observed when conventional magnesium stearate was used as the lubricant in making the tablets.

According to the present invention, the fatty acid component is dispersed into a basic aqueous solution, whereby the fatty acid component reacts with the base to form a soap. Optionally, the basic aqueous solution may be heated prior to incorporating the fatty acid component to help to prevent the fatty acid component from congealing. The alkali or alkali earth metal salt, typically magnesium sulfate or calcium sulfate, is then added and the pH is adjusted to provide an alkaline environment to raise the assay of the product by precipitation of any excess Mg as MgO.

The following-examples are given for illustrative purposes only and are not intended to limit the scope of the present invention in any way.

Manufacturing of Magnesium Stearate Mixed Hydrate

EXAMPLE 1

A magnesium stearate composition containing a variable ratio of discrete monohydrate and dihydrate polymorphs is manufactured from a "soap solution" via precipitation, as is well known in the art. The salt of this illustrative example is formed by mixing of at least one fatty acid and at least one strong base, NaOH and a magnesium salt, MgSO$_4$. In the present invention, the soap solution is produced from a fatty acid mixture of suitable stearic/palmitic acid composition to obtain an appreciable amount of the dihydrate form of the resulting stearate. Addition of the alkali earth salt to an alkaline "soap solution" results in the precipitation of magnesium stearate containing the dihydrate phase. The precipitate is separated from the liquor, and dried to a water content of 3.5-6.0%, predominately water of hydration. A fine-particulate solid is obtained. The product is designed for use as a pharmaceutical lubricant/mold release agent, but can be used for other applications, as is known in the art.

The following is an illustrative example of an industrial manufacturing process for a product containing the desired magnesium stearate dihydrate and is not intended to limit the present invention to the production of magnesium stearate/palmitate for pharmaceutical uses:

An aqueous solution, either water or a heel from a previous batch was heated to a temperature at which the fatty acid did not congeal when introduced to the aqueous solution, as is well known. A 50% sodium hydroxide solution was added in at least a 1:1 molar ratio to -the fatty acid, so that substantially all the fatty acid was converted to the sodium soap. The fatty acid component was then added until the solution was slightly alkaline to phenolphthalein indicator. In this illustrative example, a fatty acid component of about 93% by weight stearic acid to about 5% by weight palmitic acid was used.

A solution of magnesium sulfate was then added, without agitation, in an amount to substantially precipitate the sodium soap, thereby forming the magnesium stearate/palmitate. The reaction mixture was then mixed to create a homogeneous mixture and insure reaction with the magnesium sulfate, typically about 20 minutes. The reaction mixture remained heated throughout this and the remaining steps to prevent any solidification of the reaction mixture, thereby providing ease of handling. The pH was then adjusted with sodium hydroxide to precipitate any excess magnesium as MgO. An illustrative pH range is from about 9.0 to about 9.5. A solid-liquid separation was performed, and the resulting solid product was dried, and deagglomerated by suitable conventional methods. These steps and reaction conditions are well known to those skilled in the art.

This resulting product was characterized as containing a mixture of magnesium stearate and magnesium palmitate as mixed hydrates as follows:

1. The product had a loss on drying of 3.5-6.0% indicating a significant amount of the dihydrate form is present.

2. DSC analysis showed 2 endothermic transitions between 100°-135° C. (ca. 118° C. and 128° C. for Mg stearate) as a result of 2 pseudo polymorphs that are each derived from unique hydrates.

3. X-ray diffraction-showed crystallinity (not amorphous), and exhibited a characteristic XRD pattern indicating the dihydrate form is present.

The product had regular or irregular (e.g. fragmented) platelet morphology.

Other features of the manufacturing process that are considered relevant to the manufacture of magnesium stearate are obvious to those skilled in the art.

EXAMPLE 2

A magnesium stearate composition is prepared according to the method of Example 1 utilizing fatty acid having a stearic/palmitic acid ratio of at least about 10:1 and a total water content of less than about 6%. Of that 6% water, preferably 15-100% of the total water content is crystalline water dihydrate, with less than about 10% of the total water content being free water, and the remainder of the water content being monohydrate. The fatty acid stream used in this alternative embodiment contains the sum of stearate and palmitate no less than 98% of the total acid content. The pH adjustment is made to render the reaction mixture substantially neutral. The product is dried at a temperature at or below 60° C. to remove most of the bulk water resulting in a fine, crystalline powder containing the dihydrate phase as evidenced by TGA/DSC.

EXAMPLE 3

A magnesium sulfate solution is prepared by dissolving 98 grams of magnesium sulfate heptahydrate in 643 mL of water. The mixture is stirred at 80° C. until the salt is dissolved. In a separate vessel add 34 mL of 50% (w/w) NaOH to 1.13 liters of water and heat to 90° C. An alkaline sodium stearate (soap) is made by adding 181 grams of fatty acid containing 93% stearic acid and 5% pahnitic acid to the NaOH solution maintaining the temperature at 90° C. while stirring. 681 mL of water is added to the soap solution, lowering its temperature to 75° C. The magnesium sulfate solution is added to the soap solution and stirred to assure complete reaction. Once the precipitation is complete the batch is adjusted to a pH of 9.0 using 50% NaOH. The resulting solids are washed with water to remove sodium sulfate byproduct. The solids are dried at 60° C. The product contains a combination of the monohydrate and dihydrate forms of magnesium stearate palmitate.

Having described the invention in detail, those skilled in the art will appreciate that modifications may be made of the invention without departing from its' spirit and scope. Therefore, it is not intended that the scope of the invention be limited to the specific embodiments described. Rather, it is intended that the appended claims and their equivalents determine the scope of the invention.

The invention claimed is:

1. A magnesium stearate composition or calcium stearate composition comprising the reaction product of at least one fatty acid in a basic aqueous solution with at least one alkali earth metal sulfate selected from the group consisting of magnesium sulfate and calcium sulfate, the fatty acid comprising at least about 80% by weight stearic acid and at least about 5% by weight palmitic acid.

2. The composition of claim 1 wherein the fatty acid comprises about 88% by weight stearic acid and about 10% by weight palmitic acid.

3. The composition of claim 1 wherein the fatty acid comprises about 90% by weight stearic acid and about 8% by weight palmitic acid.

4. The composition of claim 1 wherein the fatty acid comprises about 93% by weight stearic acid and about 5% by weight palmitic acid.

5. A magnesium stearate composition comprising the reaction product of at least one fatty acid in a basic aqueous solution with magnesium sulfate, the fatty acid comprising at least about 80% by weight stearic acid and at least about 5% by weight palmitic acid.

6. The composition of claim 5 wherein the fatty acid comprises about 88% by weight stearic acid and about 10% by weight palmitic acid.

7. The composition of claim 5 wherein the fatty acid comprises about 90% by weight stearic acid and about 8% by weight palmitic acid.

8. The composition of claim 5 wherein the fatty acid comprises about 93% by weight stearic acid and about 5% by weight palmitic acid.

9. A method for preparing a magnesium stearate composition or calcium stearate composition comprising:
   providing a basic aqueous solution;
   incorporating at least one fatty acid comprising at least about 80% by weight stearic acid and at least about 5% by weight palmitic acid into the basic aqueous solution; and
   adding at least one alkali earth metal sulfate selected from the group consisting of magnesium sulfate and calcium sulfate, to form the magnesium stearate composition or the calcium stearate composition.

10. The method of claim 9 further including adjusting the pH to an alkaline pH after adding the at least one alkali earth metal sulfate.

11. The method of claim 9 further including performing a liquid-solid separation to recover the alkali earth metal stearate composition.

12. A magnesium stearate composition or calcium stearate composition comprising the reaction product of at least one fatty acid in a basic aqueous solution with at least one alkali earth metal sulfate selected from the group consisting of magnesium sulfate and calcium sulfate, wherein the fatty acid comprises at least about a 10:1 ratio by weight stearic acid to palmitic acid and a total water content of less than about 6%.

13. The composition of claim 12 wherein the total water content is comprised of about 15% to about 100% crystalline water dihydrate; less than about 10% free water; and a remainder being monohydrate.

14. A method for preparing a magnesium stearate composition or calcium stearate composition comprising:
providing a basic aqueous solution;
incorporating at least one fatty acid comprising at least about a 10:1 ratio by weight stearic acid to palmitic acid and a total water content of less than about 6% into the basic aqueous solution, wherein the basic aqueous solution is heated to a temperature at which the at least one fatty acid is dispersed within the basic aqueous solution; and
adding at least one alkali earth metal sulfate selected from the group consisting of magnesium sulfate and calcium sulfate, to form the magnesium stearate composition or the calcium stearate composition.

15. The method of claim 14 further including adjusting the pH to a substantially neutral pH after the at least one alkali earth metal sulfate is added.

16. The method of claim 14 further including performing a liquid solid separation to recover the alkali earth metal stearate composition.

17. The method of claim 14 further including drying the alkali earth metal stearate composition at a temperature of no more than about 60° C.

18. The method of claim 14 wherein the total water content of the fatty acid is comprised of about 15% to about 100% crystalline water dihydrate; less than about 10% free water; and a remainder being monohydrate.

19. The method of claim 9 wherein the fatty acid comprises about 88% by weight stearic acid and about 10% by weight palmitic acid.

20. The method of claim 9 wherein the fatty acid comprises about 90% by weight stearic acid and about 8% by weight palmitic acid.

21. The method of claim 9 wherein the fatty acid comprises about 93% by weight stearic acid and about 5% by weight palmitic acid.

* * * * *